United States Patent
Aoyagi et al.

[11] Patent Number: 5,999,841
[45] Date of Patent: Dec. 7, 1999

[54] APPARATUS FOR MEASURING CIRCULATING BLOOD VOLUME

[75] Inventors: Takuo Aoyagi; Michio Kanemoto; Naoki Kobayashi, all of Tokyo, Japan

[73] Assignee: Nihon Kohden Corporation, Tokyo, Japan

[21] Appl. No.: 08/916,295

[22] Filed: Aug. 22, 1997

Related U.S. Application Data

[62] Division of application No. 08/358,381, Dec. 19, 1994.

[30] Foreign Application Priority Data

Dec. 17, 1993 [JP] Japan .................................. 5-317636
Nov. 25, 1994 [JP] Japan .................................. 6-290994

[51] Int. Cl.$^6$ .............................. A61B 6/00; A61B 5/02
[52] U.S. Cl. ........................... 600/431; 600/479; 600/507
[58] Field of Search .................................. 600/481, 431, 600/479, 507, 310, 432, 473, 476, 504, 526

[56] References Cited

U.S. PATENT DOCUMENTS

| | | | |
|---|---|---|---|
| 3,677,648 | 7/1972 | Dorsch | 356/40 |
| 5,024,231 | 6/1991 | Feldschuh et al. | 600/431 |
| 5,284,137 | 2/1994 | Kessler et al. | 600/317 |
| 5,458,128 | 10/1995 | Polanyi et al. | 600/431 |
| 5,697,371 | 12/1997 | Aoyagi et al. | 600/431 |

OTHER PUBLICATIONS

A Method for Measurement of Total Circulating Blood Volume Using Indocyanine Green, Kiyoshi Haneda et al., Tohoku J. exp. Med. 1986, 148, pp. 49–56.

*Primary Examiner*—Cary O'Connor
*Assistant Examiner*—Navin Natnithithadha
*Attorney, Agent, or Firm*—Sughrue, Mion, Zinn, Macpeak & Seas, PLLC

[57] ABSTRACT

Using the principle of pulse oximetry, the relationship between the logarithm of dye density and the passage of time is obtained to determine a regression line for the linear portion of the relationship; an intial dye density in the blood is determined for the point of time that defines the mean transit time for the initial circulation of the injected dye on the regression line; and the circulating blood volume is calculated from the thus determined initial dye density.

3 Claims, 7 Drawing Sheets

APPARATUS FOR MEASURING CIRCULATING BLOOD VOLUME

This is a divisional of application Ser. No. 08/358,381, filed Dec. 19, 1994.

BACKGROUND OF THE INVENTION

1. Field of Invention

The present invention relates to an improved apparatus for measuring the circulating blood volume.

2. Related Art

The circulating blood volume is an important piece of biological information for medical diagnosis. This has conventionally been measured by a method that comprises injecting a dye that is slow in clearing from blood vessels, taking a blood sample at the point of time when the dye has been distributed uniformly throughout the blood in the whole body, measuring the dye density in the blood, and calculating the circulating blood volume from the measured dye concentration.

This method, however, has had two major disadvantages. First it requires lots of steps and time to perform one cycle of measurement; second, the residual dye in blood precludes frequent measurements. If a fast dye is used that is cleared rapidly out of the blood vessels, it is necessary to perform frequent post-injection blood sampling and a corresponding number of measurements must be made to know the dye concentration in the blood samples. Furthermore, the precision of measurements depends on the frequency of blood sampling. Because of these limitations, the use of fast dyes is by no means a practical approach.

The recent advances in electronics have made it possible to achieve noninvasive, continuous and precise measurements of dye concentration in blood by applying the principle of pulse oximetry, in which the ratio between the density of two light absorbers in arterial blood is determined on the basis of the pulsation of light transmitted through a living tissue. To measure the dye density in the blood by this method, the ratio between the densities of hemoglobin and an injected dye is first determined and then multiplied by the separately measured hemoglobin in the blood to determine the absolute value of dye density in arterial blood. The dye dilution curve, or the time-dependent changes in the absolute value of the dye density, has a definite straight line when expressed in a semi-logarithmic graph. Extrapolating this straight line to the dye injection time gives a dye density in the blood that would be obtained if the dye were distributed uniformly in total blood without being cleared from blood vessels. The thus determined dye density is named its initial dye density. Dividing the amount of the injected dye by its initial density will give circulating blood volume.

This method provides for frequent repetitions of measurement by injection of a dye that has only a short lifetime in blood. This method also enables the measurement of the clearing ability of an organ that performs selective excretion of the dye used or the blood flow in that organ.

However, this method which relies upon the principle of pulse oximetry is not free from problems. To meet the need for measuring the light transmitted through a living tissue, the site of measurement is limitted to peripheral such as an earlobe or a fingertip. Further, the dye injection site is often peripheral such as an antecubital vein and, hence, it takes a long time for the injected dye to travel from the injection site to the site of measurement. The length of this time is particularly long if massive bleeding occurs to reduce the circulating blood volume. If, under such circumstances, the straight line obtained by logarithmic transformation of the dye dilution curve is extrapolated to the injection time, the measured initial dye density will differ greatly from the actual value, creating a substantial error in measurement. With a view to eliminating this error, Haneda et al. proposed in 1986 a method for extrapolation to the dye appearance time $T_a$ (Tohoku Journal of Experimental Medicine 1986, 148 page 49–56 "A method for measurement of Total circulating blood volume using indocyanine green"). This method enables elimination of the error dependent difference in the lapse of time from $T_0$ (dye injection time) to $T_a$ (dye appearance time). For instance, the injected dye will appear after the lapse of 5 to 10 seconds when measurement is conducted at an earlobe whereas a time of 10 seconds to 2 minutes lapses when measurement is conducted at a fingertip. Nevertheless, the dye injected into the blood will mix with the blood and diffuse both forward and backward of that portion of blood. Hence; the most rapidly advancing portion of the injerted dye concentration will advance ahead of the center of the injected dye concentration as it approaches a measuring site. This phenomenon is pronounced if the peripheral blood circulation is inefficient and the time from $T_a$ to the time which is the center of the population of dye appears will sometimes be as great as 30 seconds or more if measurement is conducted at a fingertip. Thus, great errors have occasionally occurred even if extrapolation to the dye appearance time $T_a$ is made.

SUMMARY OF THE INVENTION

An object, therefore, of the present invention is to solve the aforementioned problem with the conventional practice of injecting a fast dye into a blood vessel, measuring continuously the dye density on the basis of continuous measurement of pulsation of transmitted light through a living tissue, and calculating the circulating blood volume from the time-dependent changes in the measured dye density in the blood, the problem being such that an error in measurement occurs if the exponential decay portion of the dye dilution curve is extrapolated to either the dye injection time or the dye appearance time.

The invention relates to an apparatus for measuring the circulating blood volume by injecting a predetermined amount of dye into a blood vessel in the human body, measuring the dye density in the blood continuously on the basis of continuous measurement of pulsation of transmitted light through a living tissue, and calculating the circulating blood volume from the measured dye density in the blood, comprising:

dye density measuring means for measuring the dye density in the blood continuously;

mean transit time detecting means for determining the mean transit time from the result of measurement with said dye density measuring means;

interval determining means for determining an interval for regression line calculation from the point of time as determined by said mean transit time detecting means;

logarithmic transformational means for performing logarithmic transformation of the dye density as measured by said dye density measuring means;

regression line calculating means by which a regression line for the curve that represents the relationship between the logarithm of the dye density as determined by said logarithmic transformational means and the time of measurement is determined for the interval as determined by said interval determining means;

initial dye density calculating means for determining the initial dye density by extrapolating the thus determined regression line to the point of mean transit time; and circulating blood volume calculating means for determining the circulating blood volume by dividing the amount of injected dye by the dye density as determined by said initial dye density calculating means.

In the apparatus of the present invention, the mean transit time detecting means is replaced by peak time detecting means that determines the time at which the dye density as measured by said dye density measuring means becomes maximal, and the initial density calculating means is replaced by means that determines the initial dye density by extrapolating the calculated regression line to the time at which the dye density becomes maximal.

In the apparatus of the present invention, the logarithmic transformational means is eliminated and the interval determining means, the regression line calculating means and the initial dye density calculating means are replaced respectively by the following: interval determining means for determining an interval for exponential regression curve calculation from the point of time as determined by said mean transit time detecting means; exponential regression curve calculating means by which an exponential regression curve for the curve that represents the relationship between the dye density as measured by said dye density measuring means and the time of measurement is determined for the interval as determined by said interval determining means; and initial dye density calculating means that determines the initial dye density by extrapolating the thus calculated exponential regression curve to the point of mean transit time.

In the apparatus of the present invention, the logarithmic transformational means is eliminated and the mean transit time determining means, the interval determining means, the regression line calculating means and the initial dye density calculating means are replaced respectively by the following: peak time detecting means that determines the time at which the dye density as measured by said dye density measuring means becomes maximal; interval determining means for determining an interval for exponential regression curve calculation from the point of time as determined by said peak time detecting means; exponential regression curve calculating means by which an exponential regression curve for the curve that represents the relationship between the dye density as measured by said dye density measuring means and the time of measurement is determined for the interval as determined by said interval determining means; and initial dye density calculating means that determines the initial dye density by extrapolating the thus calculated exponential regression curve to the time at which the dye concentration becomes maximal.

According to the present invention, the dye density measuring means performs continuous measurement of the dye density of the injected dye. The result of this continuous measurement is used by the mean transit time detecting means to determine the mean transit time. The interval determining means determines an interval for regression line calculation from the time as determined by the mean transit time determining means. The regression line calculating means determines, for the interval as determined by said interval determining means, a regression line for the curve that represents the relationship between the logarithm of the dye density as determined by the logarithmic transformational means and the time of measurement. The initial dye density calculating means extrapolates the thus determined regression line to the point of mean transit time and determines the dye density at the mean transit time $T_m$, or the time taken from the dye injection time $T_0$ until the mean transit time (hereunder abbreviate as MTT) of the initial circulating part of the dye has lapsed. In other words, MTT is the time taken from the injection of the dye at a given site to the time at which one half the total quantity of the dye has passed the site of measurement. The circulatory blood volume calculating means determines the circulating blood volume by dividing the amount of injected dye by the dye density as determined by said initial dye density calculating means.

According to the present invention, the dye density measuring means performs continuous measurement of the density of the injected dye. The result of this continuous measurement is used by the peak time detecting means to determine the time at which the measured dye density becomes maximal. The interval determining means determines an interval for regression line calculation from the time as determined by the peak time detecting means. The regression line calculating means determines, for the interval as determined by said interval determining means, a regression line for the curve that represents the relationship between the logarithm as determined by the logarithmic transformational means and the time of measurement. The initial dye density calculating means extrapolates the thus determined regression line to the time at which the dye density becomes maximal. The circulating blood volume calculating means determines the circulating blood volume by dividing the amount of injected dye by the dye density as determined by said initial dye density calculating means.

According to the present invention, the dye density level measuring means performs continuous measurement of the density of the injected dye. The result of this continuous measurement is used by the mean transit time detecting means to determine the mean transit time. The interval determining means determines an interval for exponential regression curve calculation from the thus determined mean transit time. The exponential regression curve calculating means determines, for the interval as determined by said interval determining means, an exponential regression,curve for the curve that represents the relationship between the dye density as measured by the dye density measuring means and the time of measurement. The initial dye density calculating means extrapolates the thus determined regression exponential curve to the point of mean transit time. The circulating blood volume calculating means determines the circulating blood volume by dividing the amount of injected dye by the dye density as determined by said initial dye density calculating means.

According to the present invention, the dye density measuring means performs continuous measurement of the density of the injected dye. The result of this continuous measurement is used by the peak time detecting means to determine the time at which the measured dye concentration becomes maximal. The interval determining means determines an interval for exponential regression curve calculation from the thus determined peak time. The exponential regression curve calculating means determines, for the interval as determined by said interval determining means, an exponential regression curve for the curve that represents the relationship between the dye density as measured by the dye density measuring means and the time of measurement. The initial dye density calculating means extrapolates the thus determined exponential regression curve to the time at which the dye density becomes maximal. The circulating blood volume calculating means determines the circulating blood volume by dividing the amount of injected dye by the dye density as determined by said initial dye density calculating means.

DETAILED DESCRIPTION OF THE PREFERRED EMBODIMENTS

Figure 1:
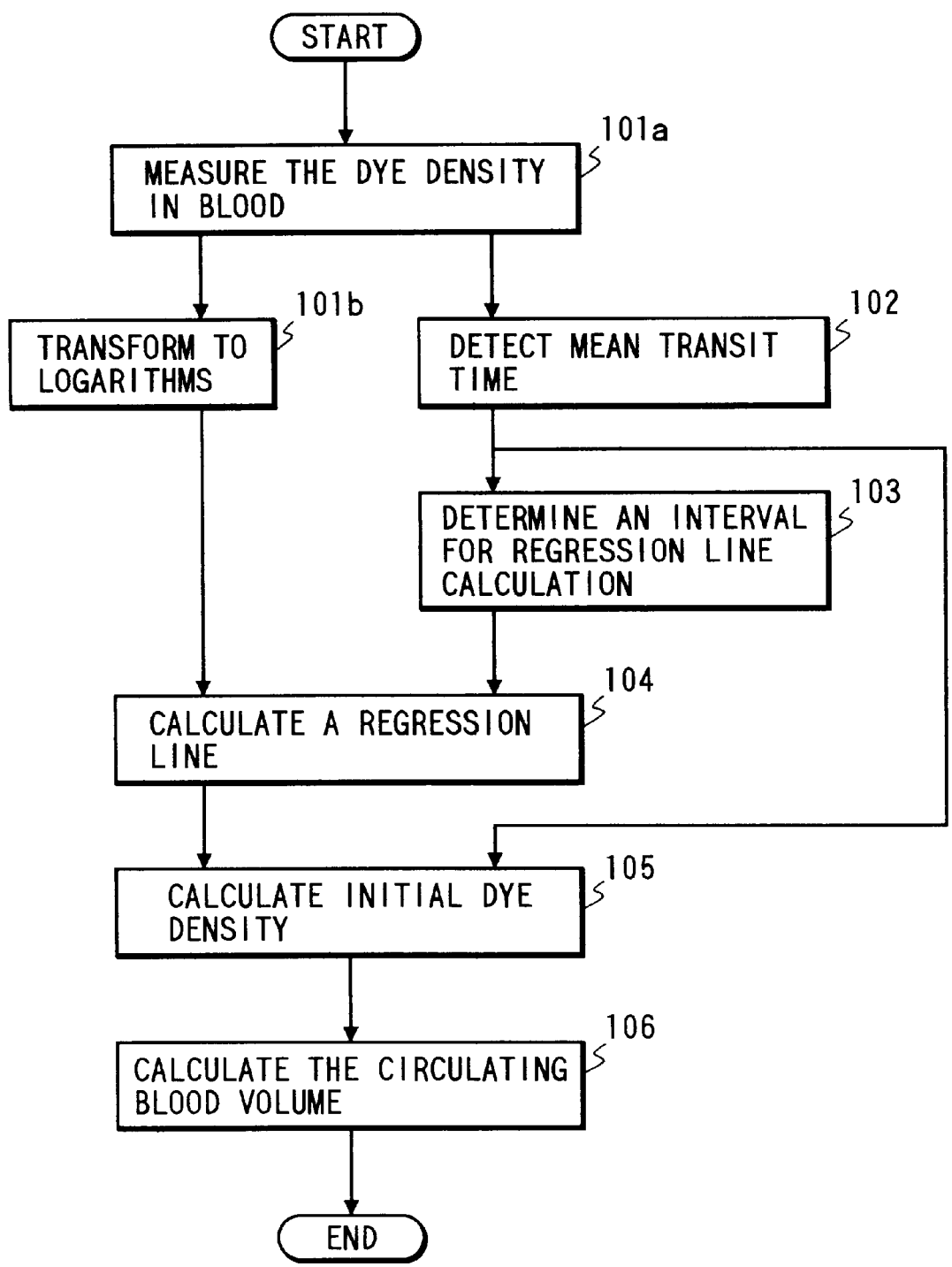
FIG. 1 is a flowchart illustrating the operational sequence of an apparatus according to the first embodiment of the invention.
Figure 2:
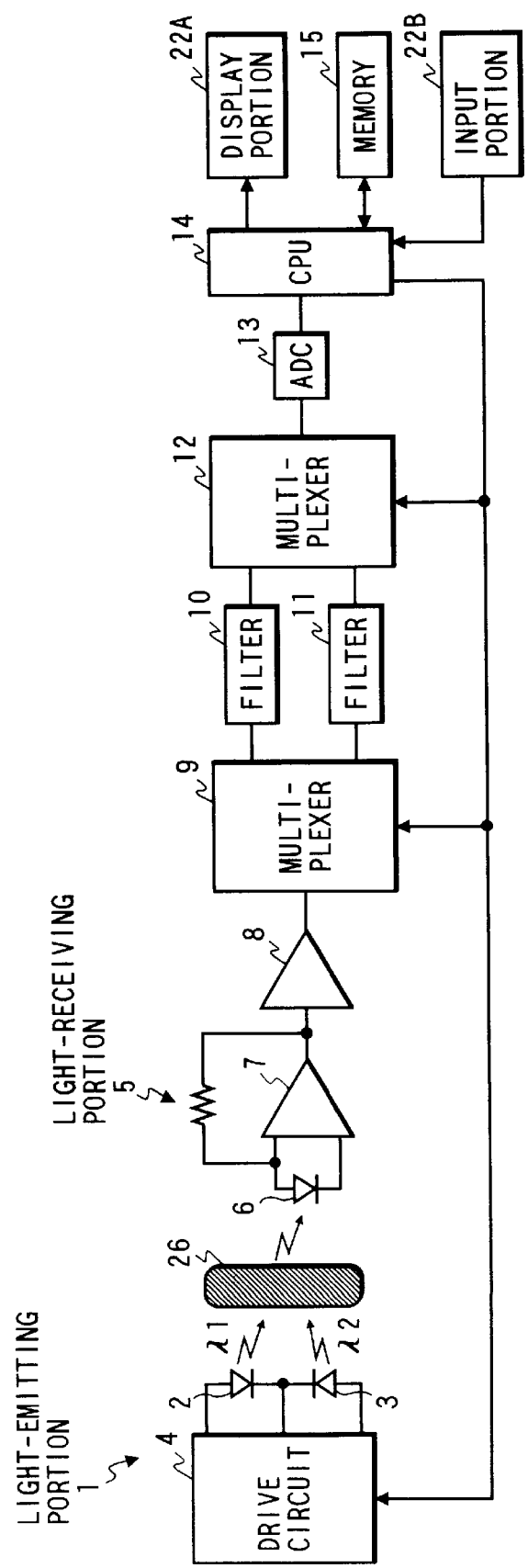
FIG. 2 is a block diagram showing the general configuration of the apparatus according to the first embodiment of the invention.

FIG. 2 is a block diagram showing the general configuration of a system according to the first embodiment of the invention. A light-emitting portion 1 consists of two LEDs 2 and 3 that emit light at two different wavelengths, and a drive circuit 4 for driving these LEDs. Assume that LED 2 emits light at wavelength $\lambda_1$ whereas LED 3 emits light at wavelength $\lambda_2$. A light-receiving portion 5 consists of a photodiode 6 placed in a face-to-face relationship with LEDs 2 and 3, a current-voltage converter 7 which converts the output current of the photodiode 6 to a voltage signal, and an amplifier 8. A multiplexer 9 is a circuit that receives a signal from the amplifier 8 and supplies it alternately to filters 10 and 11. A multiplexer 12 is a circuit that receives the outputs of filters 10 and 11 and alternately supplies them to an A/D converter 13. The A/D converter 13 is a circuit that receives an analog signal from the multiplexer 12 and converts it to a digital signal. A CPU 14 is a circuit that not only controls the drive circuit 4 and multiplexers 9 and 12 by means of control signals but also performs computations on the basis of the signal from the A/D converter 13, thereby determining the circulating blood volume. A memory 15 is a circuit that not only contains the program set forth in FIG. 1 but also stores the data that are supplied from CPU 14. CPU 14 will execute the program contained in the memory 15. A display portion 22A will display the data that are supplied from CPU 14. An input portion 22B consists of a plurality of switches and keys that are touched by the operator to produce associated input signals that are fed into CPU 14.

Figure 3:
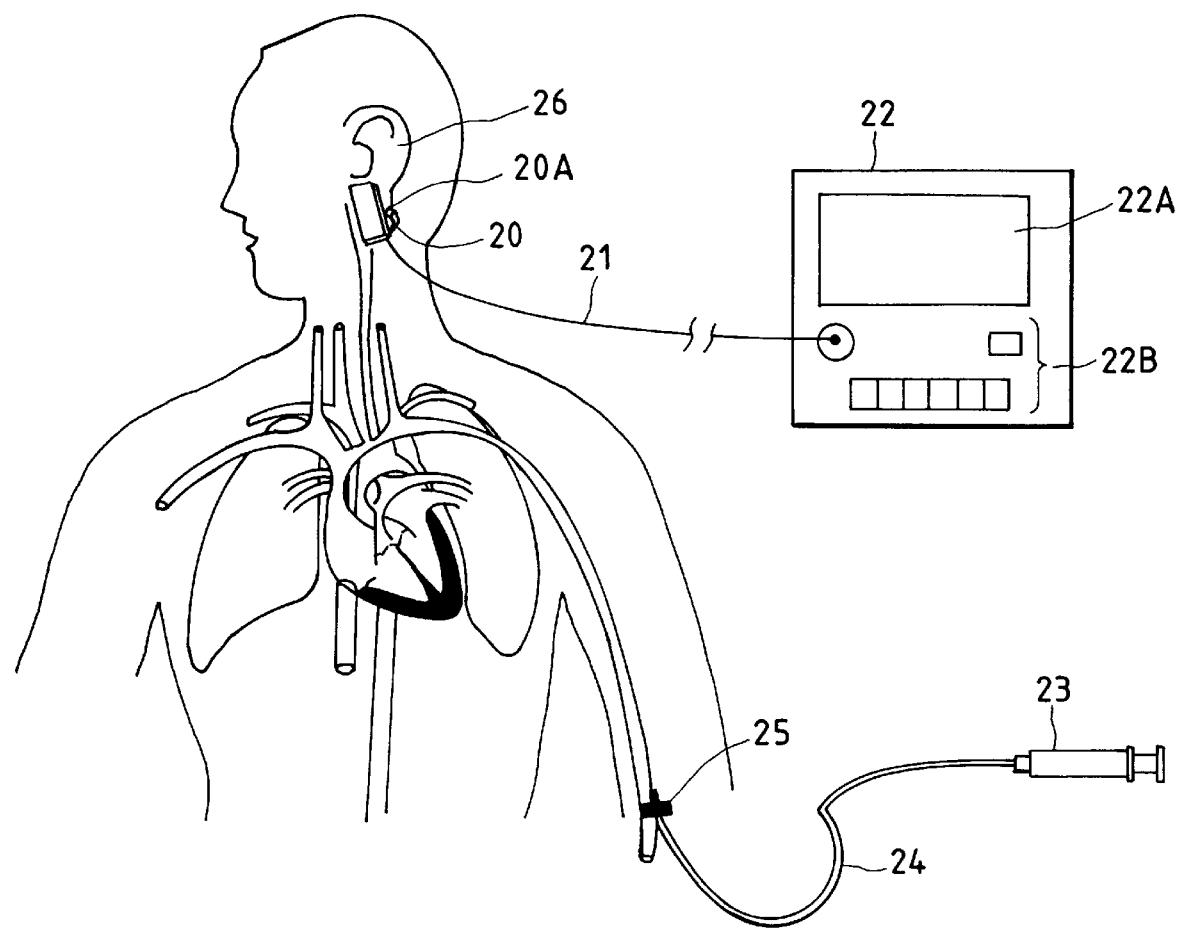
FIG. 3 is a diagram showing how the apparatus according to the first embodiment of the invention is used.

FIG. 3 shows how the apparatus according to the first embodiment of the invention is used. The probe 20 of the apparatus is fitted on an earlobe 26 of a subject. The probe 20 has a clip 20A comprising two opposing grippers. One gripper is fitted with LEDs 2 and 3 (see FIG. 2) and the other gripper is fitted with photodiode 6 also shown in FIG. 2. As one can see from FIG. 2, the light emitted from LEDs 2 and 3 will pass through the earlobe 26 to be launched into the photodiode 6. As shown in FIG. 3, LEDs 2 and 3 and photodiode 6 are connected to the main unit 22 of the apparatus via a lead wire 21. The main unit 22 has the display portion 22A and the input portion 22B exposed on the surface.

The apparatus shown in FIGS. 2 and 3 will operate in the following manner. When the operator switches the power on, CPU 14 will output control signals to the drive circuit 4 and multiplexers 9 and 12, respectively. The drive circuit 4 alternately turns on and off the LEDs 2 and 3 for predetermined periods of time. Multiplexer 9 will supply the output of amplifier 8 to filter 10 while LED 2 is on and it supplies said output to filter 11 while LED 3 is on. Filters 10 and 11 eliminate the noise in the signals from light having wavelengths $\lambda_1$ and $\lambda_2$, respectively. The multiplexer 12 alternately supplies the noise-free signals to the A/D converter 13, which digitizes those signals before they enter the CPU 14. The operator injects a dye such as ICG (indocyanine green) from a syringe 23 (see FIG. 3) into the subject at a peripheral site, say, an antecubital vein via a conduit 24 and a catheter 25. Simultaneously with the dye injection, the operator touches a relevant switch to signal the injection start time to CPU 14.

The subsequent procedure will now be described with reference to the flowchart shown in FIG. 1. In step 101a, CPU 14 calculates $C_g$, or the dye density of ICG in the blood, on the basis of the signal supplied from the A/D converter 13. Calculation of $C_g$ is performed in accordance with the following equation (A):

$$C_g = [\log\{I_{\lambda 1}/(I_{\lambda 1}-\Delta I_{\lambda 1})\}/\log\{I_{\lambda 2}/(I_{\lambda 2}-\Delta I_{\lambda 2})\} - (K_1/K_2)] \cdot (K_2/K_3) \cdot K_4 \quad (A)$$

where $I_{\lambda 1}$ is the quantity of transmitted light at wavelength $\lambda_1$ and $I_{\lambda 2}$ is the quantity of transmitted light at wavelength $\lambda_2$, and both are the values of the signals supplied from A/D converter 13 to CPU 14; $\Delta I_{\lambda 1}$ and $\Delta I_{\lambda 2}$ are the values that are determined from the changes in $I_{\lambda 1}$ and $I_{\lambda 2}$, respectively, and which are detected with CPU 14; $K_1$, $K_2$, $K_3$ and $K_4$ are the values that are loaded in CPU 14 and which are adjustable by key entry.

Equation (A) is used in the invention for the following reasons.

First, the Lambert-Beer law states that the following equation holds in the case where a dye-containing substance is illuminated with light:

$$E \cdot C \cdot D = \log(Iin/I) \quad (1)$$

where E is the extinction coefficient of the dye; C is the density of the dye; D is the thickness of the dye-containing substance; $I_{in}$ is the quantity of incident light; and I is the quantity of transmitted light.

The relationship expressed by equation (1) is valid as an approximation for a light-scattering substance such as blood and the error that may occur will not affect the essence of the present invention. Therefore, the following discussion presupposes the validity of equation (1). When a living tissue containing a pulsating blood flow is illuminated with light, the following equation will hold (the suffix b refers to the blood layer and the suffix t to the tissue layer excepting the blood layer):

$$E_b \cdot C_b \cdot D_b + E_t \cdot C_t \cdot D_t = \log(Iin/I) \quad (2)$$

If the thickness of the blood layer $D_b$ increases by $\Delta D_b$ due to pulsation, the quantity of transmitted light will decrease by $\Delta I$; hence, the following equation holds:

$$E_b \cdot C_b \cdot (D_b + \Delta D_b) + E_t \cdot C_t \cdot D_t = \log\{Iin/(I-\Delta I)\} \quad (3)$$

Subtracting eq. (2) from eq. (3), we get:

$$E_b \cdot C_b \cdot \Delta D_b = \log\{I/(I-\Delta I)\} \quad (4)$$

If the blood contains the injected dye, the following equation will hold:

$$E_b \cdot C_b \cdot \Delta D_b + E_g \cdot C_g \cdot \Delta D_b = \log\{I/(I-\Delta I)\} \quad (5)$$

where $E_b$ is the extinction coefficient of the blood; $C_b$ is the density of hemoglobin (light absorption by the blood is due to the hemoglobin in blood); $E_g$ is the extinction coefficient of the injected dye; and $C_g$ is the density of the injected dye.

If the light having wavelength $\lambda_1$ is absorbed by both the blood and the injected dye as in the case where $\lambda_1$ is 805 nm, eq. (5) is rewritten as:

$$E_{b\lambda 1} \cdot C_b \cdot \Delta D_b + E_{g\lambda 1} \cdot C_g \cdot \Delta D_b = \log\{I_{\lambda 1}/(I_{\lambda 1}-\Delta I_{\lambda 1})\} \quad (6)$$

If the light having wavelength $\lambda_2$ is absorbed by the blood but not by the injected dye as in the case where $\lambda_2$ is 900 nm, eq. (5) is rewritten as:

$$E_{b\lambda 2} \cdot C_b \cdot \Delta D_b = \log\{I_{\lambda 2}/(I_{\lambda 2}-\Delta I_{\lambda 2})\} \quad (7)$$

Combining eqs. (6) and (7), we get:

$$(E_{b\lambda 1}/E_{b\lambda 2}) + (E_{g\lambda 1}/E_{b\lambda 2}) \cdot (C_g/C_b) = \log\{I_{\lambda 1}/(I_{\lambda 1}-\Delta I_{\lambda 1})\}/\log\{I_{\lambda 2}/(I_{\lambda 2}-\Delta I_{\lambda 2})\} \quad (8)$$

Hence, $C_g$ is expressed by:

$$C_g = [\log\{I_{\lambda 1}/(I_{\lambda 1}-\Delta I_{\lambda 1})\}/\log\{I_{\lambda 2}/(I_{\lambda 2}-\Delta I_{\lambda 2})\} - (E_{b\lambda 1}/E_{b\lambda 2})] \cdot (E_{b\lambda 2}/E_{g\lambda 1}) \cdot C_b \quad (9)$$

Since $C_b$ is substantially invariable using the measurement of a dilution curve for the injected dye, it may well be considered as constant and a premeasured value can be substituted. As for $E_{b\lambda 1}$ and $E_{b\lambda 2}$, the effect of the oxygen saturation is negligible, so values for 100% oxygen saturation (which are known) may be substituted. $E_{g\lambda 1}$ is predetermined for the specific dye to be used and hence is known. With these values stored in memory, $\Delta I_{\lambda 1}$ and $\Delta I_{\lambda 2}$ are determined from the measured values of $I_{\lambda 1}$ and $I_{\lambda 2}$. Substituting all relevant values into eq. (9), we get a dye dilution curve plotting the time-dependent values of $C_g$. Thus, $K_1$, $K_2$, $K_3$ and $K_4$ in eq. (A) are $E_{b\lambda 1}$, $E_{b\lambda 2}$, $E_{g\lambda 1}$ and $C_b$, respectively. For each occurrence of pulsation, CPU 14 determines $\Delta I_{\lambda 1}$ and $\Delta I_{\lambda 2}$ and calculates eq. (A). This procedure gives a dye dilution curve, or the continuum of varying values of $C_g$. Each time it gets the value of $C_g$, CPU 14 also determines its logarithm by calculation. This step of logarithmic transformation is labelled step 101b in FIG. 1. CPU 14 loads memory 15 with data on the thus determined two kinds of dye dilution curve (one representing the relationship between $C_g$ and time t and the other representing the relationship between log $C_g$ and time t).

Figure 4:
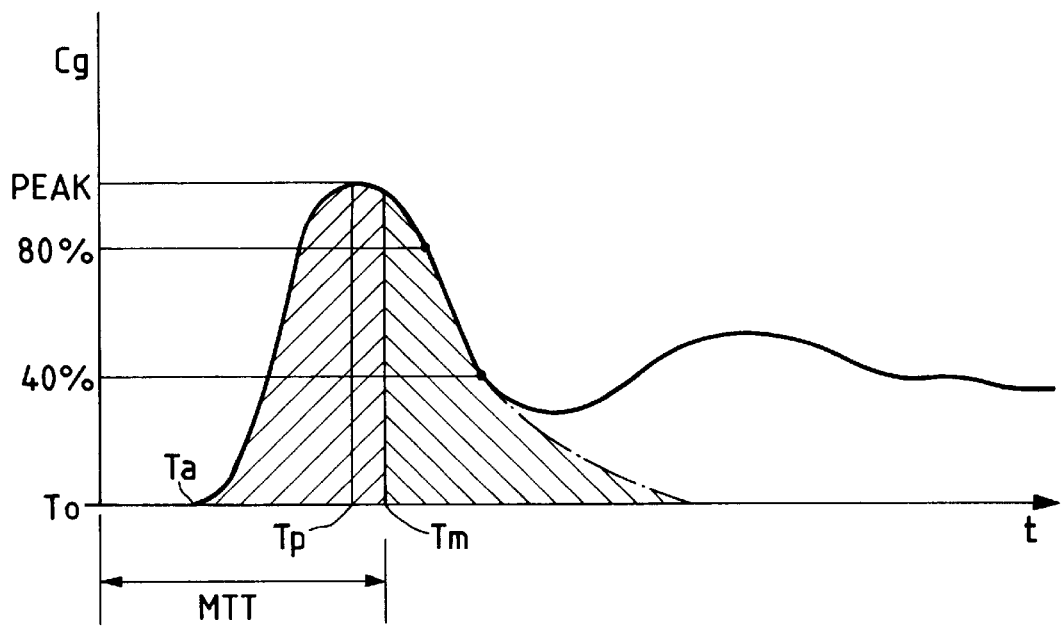
FIG. 4 is a graph showing the dye density vs time relationship as measured with the apparatus according to the first embodiment of the invention.

Processing with CPU 14 proceeds to step 102 for calculating the mean transit time MTT by the following procedure. First, an initial circulation curve is determined using the $C_g$-t curve (see FIG. 4) which is stored in memory 15. To this end, two points on the $C_g$-t curve are selected, one at 80% of the first peak value and the other at 40% of the peak value; then, an exponential attenuation curve is drawn that passes through these two points. The thus determined exponential curve is combined with a $C_g$-t curve starting at zero $C_g$ past the first peak and ending at 80% of that peak value, thereby constructing the initial circulation curve. In the next step, the total area defined by this initial circulation curve and the t-axis is determined and bisected by a straight line parallel to the $C_g$-axis; the point at which this straight line crosses the t-axis represents the MTT and the value of t at that point is named $T_m$.

Figure 5:
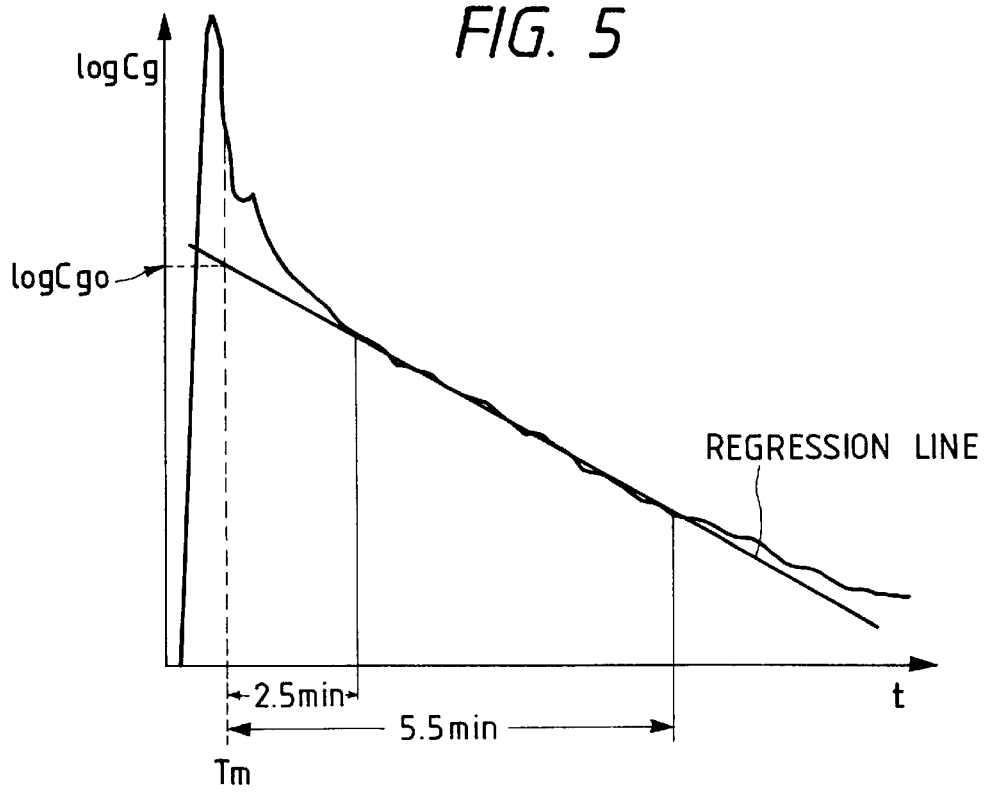
FIG. 5 is a graph showing the logarithm of dye density vs time relationship as measured with the apparatus according to the first embodiment of the invention.

Processing with CPU 14 then proceeds to step 103 for determining an interval for calculating a regression line for the log $C_g$-t curve (see FIG. 5) which is also stored in memory 15. The interval to be calculated is defined by two points of time t, one at 2.5 min after the $T_m$ which has been determined in step 102 and the other at 5.5 min after the $T_m$. Thus, CPU 14 calculates both $T_m+2.5$ (min) and $T_m+5.5$ (min) and holds the result of calculation.

Processing with CPU 14 progresses to step 104 for calculating a regression line based on the interval data that have been determined in previous step 103. Stated more specifically, the line of regression is expressed by log $C_g=at+b$ (see FIG. 5) and the coefficients a and b are determined by the method of least squares.

Processing with CPU 14 then goes to step 105 for calculating the initial dye density. Stated more specifically, the regression line that has been determined in step 104 is extrapolated to the time $T_m$ and log $C_{g0}$, or the value of log $C_g$ at $T_m$, is determined. The inverse log of this value is $C_{g0}$.

Processing with CPU 14 proceeds to step 106 for calculating the circulating blood volume. In this step, the amount of injected dye is divided by $C_{g0}$ which has been determined in step 105. The amount of injected dye was preliminarily supplied to and held by CPU 14 before the process started. As a result of this final step, the circulating blood volume is determined and displayed in the display portion 22A.

In accordance with the first embodiment of the invention described above, MTT is determined from the total area of the initial circulation curve and this gives the correct value of MTT.

After MTT is thus determined, extrapolation to the mean transit time $T_m$ is made to determine the initial dye concentration, which is further processed to determine the circulating blood volume. Determining the time $T_m$ in this method requires that the correct value of the mean transit time MTT be obtained. To this end, the initial circulating portion of the dye has to be isolated correctly from the dye density diagram. However, if the peripheral blood circulation is inefficient, the injected dye will be diffused in both forward and backward directions and the overlap between the density waveforms of the initial and recirculating portions of the dye will sometimes introduce difficulty into the operation of isolating the initial circulating portion by calculation. In a case like this, extrapolation may be effected to the peak density time $T_p$ which substantially coincides with the time $T_m$.

Figure 6:
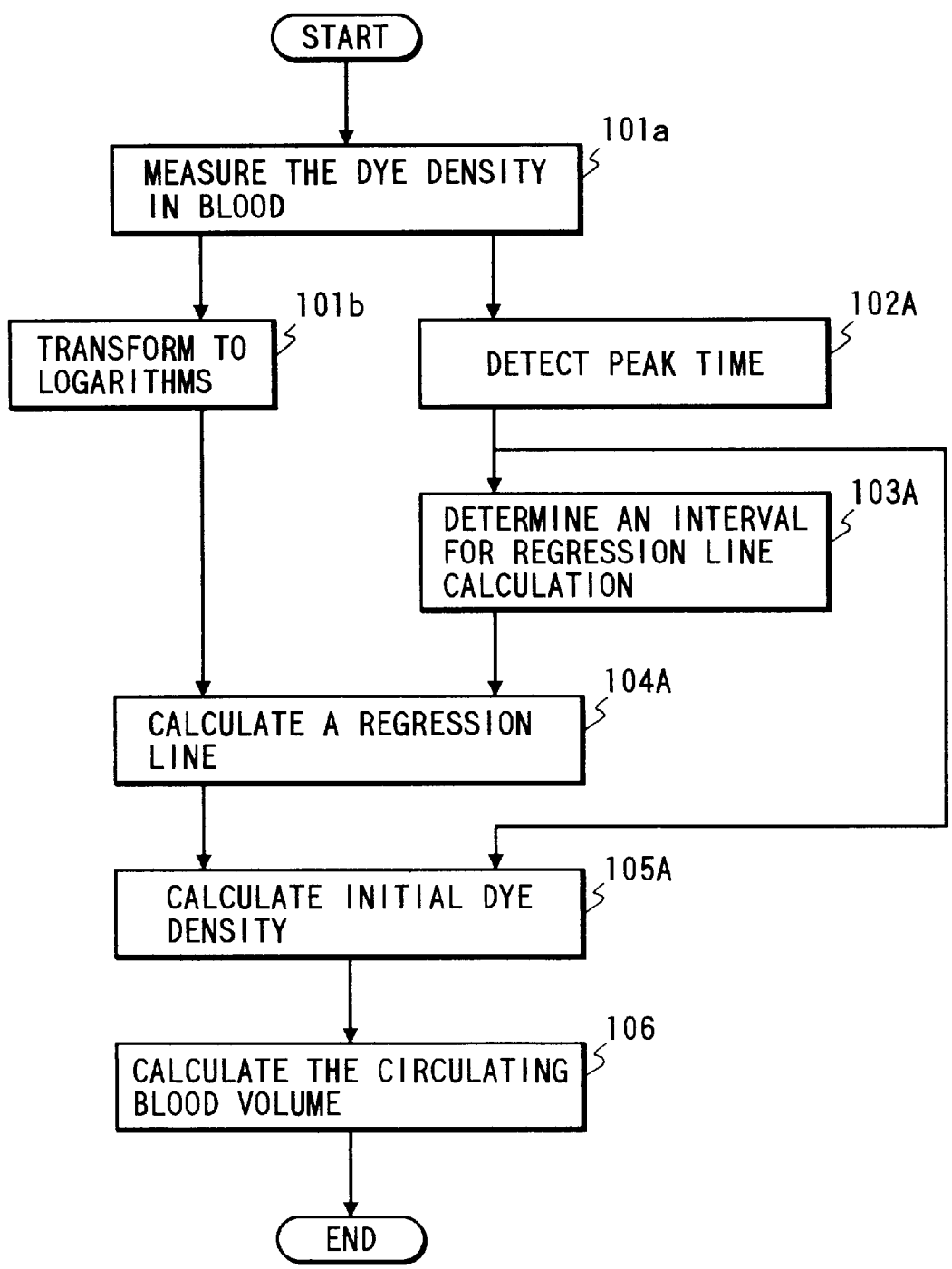
FIG. 6 is a flowchart illustrating the operational sequence of an apparatus according to the second embodiment of the invention.

Thus, the second embodiment of the invention relates to an apparatus in which the time $T_m$ is replaced by the peak density time $T_p$, or the point of time at which the dye dilution curve assumes a peak value. The composition of the apparatus according to the second embodiment is essentially the same as that of the apparatus according to the first embodiment, except that CPU 14 performs processing according to the flowchart shown in FIG. 6. Steps 101a, 101b and 106 in this flowchart are identical to the corresponding steps in the flowchart shown in FIG. 1 and, hence, need not be described. In step 102A, CPU 14 determines $T_p$ (the time at which $C_g$ peaks) from the $C_g$-t curve stored in memory 15. In step 103A, CPU 14 determines two points of time at which two predetermined periods of time lapse from $T_p$, thereby determining an interval for regression line calculation. In step 104A, CPU 14 determines, for the thus determined interval, a regression line for the log $C_g$-t curve by calculation. In step 105A, CPU 14 extrapolates the thus determined regression line to $T_p$, determines log $C_{g0}$ (the value of log $C_g$ at $T_p$), and calculates $C_{g0}$, the inverse log of log $C_{g0}$.

The apparatus according to the second embodiment is more error prone than the apparatus according to the first embodiment but can be substituted for the latter in the case where the initial circulating portion of the dye dilution curve is not clearly distinguishable from the recirculating portion.

Figure 7:
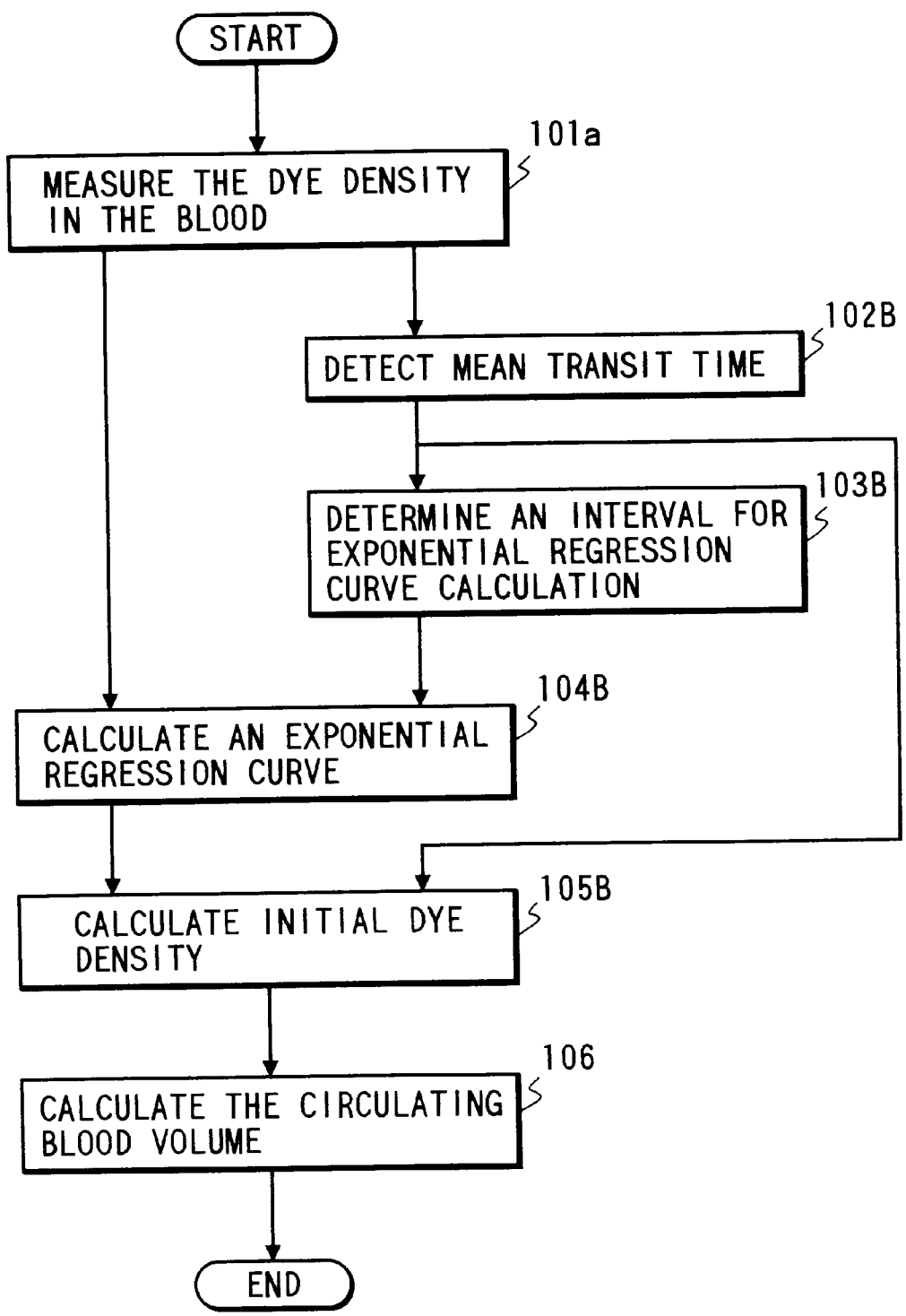
FIG. 7 is a flowchart illustrating the operational sequence of an apparatus according to the third embodiment of the invention.

In the two embodiments described above, the dye density in the blood is transformed to its logarithm and a regression line is calculated for the logarithmic data. In the third embodiment of the invention, the dye density in the blood is not transformed to the logarithm but an exponential regression curve is calculated from the $C_g$-t curve. Then, the initial dye concentration $C_{g0}$ is determined from the calculated curve and the circulating blood volume is determined from the $C_{g0}$. An apparatus according to this third embodiment will now be described. The configuration of this apparatus is essentially the same as that of the apparatus according to the first embodiment, except that CPU 14 performs processing according to the flowchart shown in FIG. 7. Steps 101a and 106 in this flowchart are identical to the corresponding steps in the flowchart shown in FIG. 1 and, hence, need not be described. Without performing logarithmic transformation of $C_g$, the embodiment under consideration does not involve a step corresponding to step 101b shown in FIG. 1. In step 102B, CPU 14 determines the time $T_m$. In step 103B, CPU determines two points of time at which two predetermined periods of time elapse from $T_m$, thereby determining an exponential regression curve. In step 104B, CPU 14 determines, for the thus determined interval, an exponential regression curve for the $C_g$-t curve by calculation. In step 105B, CPU 14 extrapolates the thus determined exponential regression curve to $T_m$ and determines $C_{g0}$, or the value of $C_g$ at $T_m$.

Figure 8:
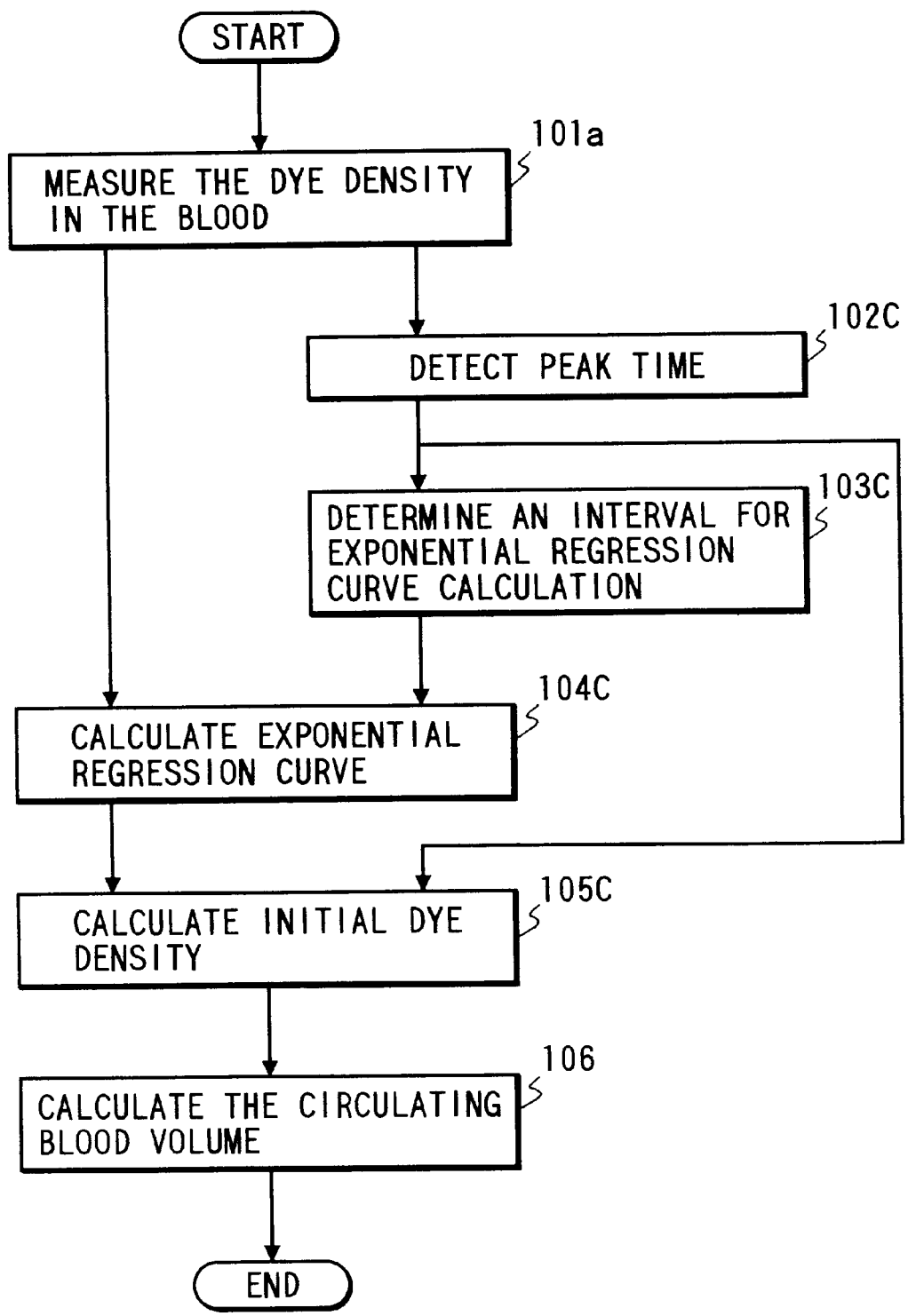
FIG. 8 is a flowchart illustrating the operational sequence of an apparatus according to the fourth embodiment of the invention.

The fourth embodiment of the invention will now be described. The configuration of an apparatus according to this fourth embodiment is essentially the same as that of the apparatus according to the first embodiment, except that CPU 14 performs processing according to the flowchart shown in FIG. 8. Steps 101a and 106 in this flowchart are identical to the corresponding steps in the flowchart shown in FIG. 1 and, hence, need not be described. Without performing logarithmic transformation of $C_g$, the embodiment under consideration does not involve a step corresponding to step 101b shown in FIG. 1. In step 102C, CPU 14 determines $T_p$ (the time at which $C_g$ peaks) from the $C_g$-t curve stored in memory 15. In step 103C, CPU 14 determines two points of time at which two predetermined periods of time lapse from $T_p$, thereby determining an interval for exponential regression curve calculation. In step 104C, CPU 14 determines, for the thus determined interval, an exponential regression curve for the $C_g$-t curve by calculation. In step 105C, CPU 14 extrapolates the thus determined regression line to $T_p$ and determines $C_{g0}$, or the value of $C_g$ at $T_p$.

The dye that is injected into blood in the four embodiments described above is ICG which is specifically cleared from the liver. It should, however, be noted that dyes that are specifically cleared from other internal organs such as kidneys may be used and similar results can be attained by performing similar processing. To determine the blood flow through the respective organs, a time constant ($\tau=-1/a$) is determined from the relevant regression lines and the circulating blood volume may be divided by the time constant.

According to the present invention, the point of time at which MTT has lapsed is used as an effective time of injection at the site of measurement and this enables correct determination of the initial density and, hence, the circulating blood volume.

According to the present invention, the point of time at which the dye concentration peaks is used as an effective time of injection at the site of measurement and this enables positive determination of the initial dye density and, hence, the circulating blood volume.

According to the present invention, the point of time at which MTT has lapsed is used as an effective time of injection at the site of measurement and this enables correct determination of the initial dye density and, hence, the circulating blood volume. As a further advantage, the elimination of logarithmic transformational means contributes to simplify the overall configuration of the apparatus.

According to the present invention, the point of time at which the dye density peaks is used as an effective time of injection at the site of measurement and this enables positive determination of the initial dye density and, hence, the circulating blood volume. As a further advantage, the elimination of logarithmic transformational means contributes to simplify the overall configuration of the apparatus.

What is claimed is:

1. An apparatus for determining a circulating blood volume comprising:

dye density measuring means for continuously measuring dye density of an infected dye in said circulating blood;

time detecting means for identifying a point of time corresponding to a predetermined dye density characteristic based on results of measurements of said dye density measuring means;

interval determining means for determining a first and a second interval point for exponential regression curve calculation based on said point of time identified by said time detecting means;

exponential regression curve calculating means for calculating an exponential regression curve for a curve that represents a relationship between said dye density measured by said dye density measuring means and time, wherein said exponential regression curve passes through said first and second interval points as determined by said interval determining means;

initial dye density calculating means for determining a dye density corresponding to an initial dye density by extrapolating said exponential regression curve at least to the point of said time identified by said time detecting means; and circulating blood volume calculating means for determining said circulating blood volume by dividing an amount of said injected dye by said initial dye density which is determined by said initial dye density calculating means.

2. An apparatus as claimed in claim 1, wherein said time detecting means identifies a point of time where the dye density reaches a mean value.

3. An apparatus as claimed in claim 1, wherein said time detecting means identifies a point of time where the dye density becomes maximal.

* * * * *